United States Patent
Gerdes et al.

(10) Patent No.: US 6,251,899 B1
(45) Date of Patent: Jun. 26, 2001

(54) METHOXIMINOMETHYLOXADIAZINES

(75) Inventors: Peter Gerdes, Aachen; Herbert Gayer, Monheim; Ulrich Heinemann, Leichlingen; Bernd-Wieland Krüger, Bergisch Gladbach; Astrid Mauler-Machnik, Leichlingen; Gerd Hänssler, Leverkusen; Klaus Stenzel, Düsseldorf, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/485,379

(22) PCT Filed: Aug. 1, 1998

(86) PCT No.: PCT/EP99/04821
§ 371 Date: Feb. 8, 2000
§ 102(e) Date: Feb. 8, 2000

(87) PCT Pub. No.: WO99/09026
PCT Pub. Date: Feb. 25, 1999

(30) Foreign Application Priority Data

Aug. 14, 1997 (DE) .............................. 197 35 196
Aug. 29, 1997 (DE) .............................. 197 37 723

(51) Int. Cl.[7] .................. C07D 413/10; A01N 43/88
(52) U.S. Cl. .................. 514/229.2; 544/66; 549/467
(58) Field of Search .................. 514/229.2; 544/66; 549/467

(56) References Cited

U.S. PATENT DOCUMENTS 5,773,445  6/1998  Gayer et al. .................. 514/269

FOREIGN PATENT DOCUMENTS

846691 A1 * 11/1997 (EP) .
96/25406 A1 * 8/1996 (WO) .
97/46542 A1 * 12/1997 (WO) .

OTHER PUBLICATIONS

Chem. Ber. 30, (Month Unavailable) 1897, pp. 1077–1087, Friedlaender et al, "Mittheilungen".

Chem. Ber. 90, (Month Unavailable), 1957, pp. 942–951, Bredereck, et al, "Formamid-Reaktionen, VIII, Eine Neue Pyrimidin-Synthese".

J. Chem. Soc., (Month Unavailable), 1955, pp. 3478–3480, Chesterfield et al, "Pyrimidines Part VIII, Halogeno–and Hydrazino–Pyrimidines".

ESC Directive 79/831, Annex 1979.

* cited by examiner

*Primary Examiner*—Richard L. Raymond
*Assistant Examiner*—Thomas McKenzie
(74) *Attorney, Agent, or Firm*—Joseph C. Gil

(57) ABSTRACT

A compound of the formula (I)

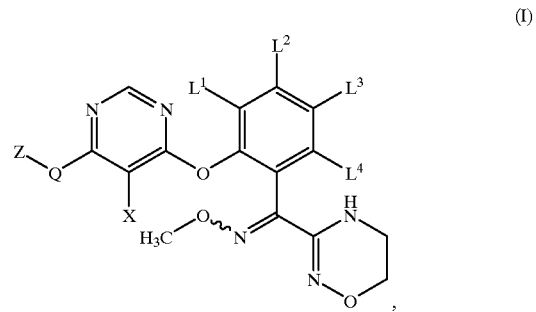

wherein

Z represents a moiety selected from the group consisting of cycloalkyl having 3 to 7 carbon atoms in the cycloalkyl moiety or cycloalkylalkyl having 3 to 7 carbon atoms in the cycloalkyl moiety and 1 to 4 carbon atoms in the alkyl moiety, with said cycloalkyl or cycloalkylalkyl being in each case optionally mono- to pentasubstituted by halogen or alkyl;

a heterocyclyl group selected from the group consisting of thienyl, pyridyl, furyl, thienylmethyl, pyridylmethyl or furylmethyl, each of which is optionally substituted by halogen, dialkylamino or alkyl having 1 to 4 carbon atoms;

an aryl or arylalkyl having in each case 6 to 10 carbon atoms in the aryl moiety and 1 to 4 carbon atoms in Q represents oxygen or sulphur, X represents halogen and The compositions have microbicidal activity.

10 Claims, No Drawings

METHOXIMINOMETHYLOXADIAZINES

This application is the National Stage Application of PCT/EP98/04821, which claims priority from German Application 197 35 196.4, filed Aug. 14, 1997 and from German Application 197 37 723.8, filed Aug. 29, 1997.

TECHNICAL FIELD OF THE INVENTION

The invention relates to novel methoximinomethyloxadiazines, to two processes for their preparation and to their use as pesticides, and also to novel intermediates and to processes for their preparation.

BACKGROUND OF THE INVENTION

It is already known that certain methoximinomethyloxadiazines have fungicidal activity (WO 96-25406). However, the activity of these prior-art compounds, in particular at low application rates and concentrations, is not entirely satisfactory in all areas of use.

DETAILED DESCRIPTION OF THE INVENTION

This invention, accordingly, provides the novel methoximinomethyloxadiazines of the general formula (I)

(I)

in which
Z represents cycloalkyl, aryl, arylalkyl, heterocyclyl or heterocyclylalkyl, each of which is optionally substituted,
Q represents oxygen or sulphur,
X represents halogen,
$L^1$, $L^2$, $L^3$ and $L^4$ are identical or different and, independently of one another, each represents hydrogen, halogen, cyano, nitro, or represents alkyl, alkoxy, alkylthio, alkylsulphinyl or alkylsulphonyl, each of which is optionally substituted by halogen.

In the definitions, the saturated or unsaturated hydrocarbon chains, such as alkyl, alkanediyl, alkenyl or alkinyl, are in each case straight-chain or branched, including in combination with heteroatoms, such as, for example, in alkoxy, alkylthio or alkylamino.

Aryl represents aromatic, mono- or polycyclic hydrocarbon rings, such as, for example, phenyl, naphthyl, anthranyl, phenanthryl, preferably phenyl or naphthyl, in particular phenyl.

Heterocyclyl represents saturated or unsaturated, and also aromatic, annular compounds in which at least one ring member is a heteroatom, i.e. an atom which is different from carbon. If the ring contains a plurality of heteroatoms, these can be identical or different. Preferred heteroatoms are oxygen, nitrogen or sulphur. If the ring contains a plurality of oxygen atoms, these are not adjacent. If appropriate, the annular compounds form, together with other carbocylic or heterocyclic, fused or bridged rings, a polycyclic ring system. Preference is given to mono- or bicyclic ring systems, in particular to mono- or bicyclic aromatic ring systems.

Cycloalkyl represents saturated carbocyclic annular compounds which may form, together with other carbocyclic, fused or bridged rings, a polycyclic ring system.

Furthermore, it has been found that the novel methoximinomethyloxadiazines of the general formula (I) are obtained when a) 3-(2-hydroxy-phenyl)-3-methoxyiminomethyl-oxadiazines of the formula (II), (II)

in which
$L^1$, $L^2$, $L^3$ and $L^4$ are each as defined above,
are reacted with a substituted halogenopyrimidine of the general formula (III), (III)

in which
Z, Q and X are each as defined above and
$y^1$ represents halogen,
if appropriate in the presence of a diluent, if appropriate in the presence of an acid acceptor and if appropriate in the presence of a catalyst, or b) phenoxypyrimidines of the general formula (IV)

(IV)

in which
X, $L^1$, $L^2$, $L^3$ and $L^4$ are each as defined above and
$y^2$ represents halogen,
are reacted with a ring compound of the general formula (V),

Z—Q—H  (V)

in which

Z and Q are each as defined above,
if appropriate in the presence of a diluent, if appropriate in the presence of an acid acceptor and if appropriate in the presence of a catalyst.

Finally, it has been found that the novel methoximinomethyloxadiazines of general formula (I) have very potent fungicidal activity.

The compounds according to the invention may be present as mixtures of different possible isomeric forms, in particular of stereoisomers, such as, for example, E and Z. Both the E and the Z isomers, and any mixtures of these isomers, are claimed.

The invention preferably provides compounds of the formula (I) in which

Z represents cycloalkyl or cycloalkylalkyl having in each case 3 to 7 carbon atoms in the cycloalkyl moiety and 1 to 4 carbon atoms in the alkyl moiety and being in each case optionally mono- to pentasubstituted by halogen or alkyl;

represents heterocyclyl or heterocyclylalkyl having in each case 3 to 7 ring members and 1 to 4 carbon atoms in the alkyl moiety and being in each case optionally substituted by halogen or alkyl having 1 to 4 carbon atoms;

or represents aryl or arylalkyl having in each case 6 to 10 carbon atoms in the aryl moiety and 1 to 4 carbon atoms in the alkyl moiety and being in each case optionally mono- to tetrasubstituted in the aryl moiety by identical or different substituents, the possible substituents preferably being selected from the list below:

halogen, cyano, nitro, amino, formyl, carbamoyl, thiocarbamoyl;

alkyl, alkoxy, alkoxyalkyl, alkylthioalkyl, alkylaminoalkyl, dialkylaminoalkyl, alkylthio, alkylsulphinyl or alkylsulphonyl having in each case 1 to 8 carbon atoms and being in each case straight-chain or branched;

alkenyl or alkenyloxy having in each case 2 to 6 carbon atoms and being in each case straight-chain or branched;

halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms and being in each case straight-chain or branched;

halogenoalkenyl or halogenoalkenyloxy having in each case 2 to 6 carbon atoms and 1 to 11 identical or different halogen atoms and being in each case straight-chain or branched;

alkylamino, dialkylamino, alkylcarbonyl, alkoxycarbonyl, alkylamino-carbonyl, dialkylaminocarbonyl, dialkylaminocarbonyl, arylalkylamino-carbonyl, alkenylcarbonyl or alkinylcarbonyl having 1 to 6 carbon atoms in the hydrocarbon chains in question and being in each case straight-chain or branched;

cycloalkyl or cycloalkyloxy having in each case 3 to 6 carbon atoms;

alkylene having 3 or 4 carbon atoms, oxyalkylene having 2 or 3 carbon atoms or dioxyalkylene having 1 or 2 carbon atoms, each of which is doubly attached and each of which is optionally mono- to tetrasubstituted by identical or different substituents selected from the group consisting of fluorine, chlorine, oxo, methyl, trifluoromethyl and ethyl;

or a grouping

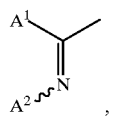

in which $A^1$ represents hydrogen or alkyl having 1 to 4 carbon atoms or cycloalkyl having 3 to 6 carbon atoms and $A^2$ represents hydroxyl, amino, methylamino, methyl, phenyl, benzyl, alkoxy, alkylamino, dialkylamino having 1 to 4 carbon atoms in the alkyl chains in question, Q represeents oxygen or sulphur, X represents fluorine, chlorine or bromine, preferably represents fluorine or chlorine and in particular represents fluorine and $L^1$, $L^2$, $L^3$ and $L^4$ are identical or different and, independently of one another another, each represents hydrogen, halogen, cyano, nitro, or represent alkyl, alkoxy, alkylthio, alkylsulphinyl or alkylsulphonyl having in each case 1 to 6 carbon atoms and being in each case optionally substituted by 1 to 5 halogen atoms, preferably represents hydrogen or methyl and in particular represents hydrogen.

The invention in particular relates to compounds of the formula (I), in which

Z represents cyclobutyl, cyclopentyl or cyclohexyl, each of which is optionally mono- to pentasubstituted by fluorine, chlorine, methyl or ethyl;

represents thienyl, pyridyl, furyl, thienylmethyl, pyridylmethyl or furylmethyl, each of which is optionally substituted by methyl, ethyl, fluorine, chlorine or bromine;

or represents phenyl or benzyl, each of which is optionally mono- to tetrasubstituted by identical or different substituents, the possible substituents being selected from the list below:

fluorine, chlorine, bromine, cyano, nitro, amino, formyl, carbamoyl, thio-carbamoyl, methyl, ethyl, n- or i-propyl n-, i-, s- or t-butyl, methoxymethyl, methoxy, ethoxy, n- or i-propoxy, methylthio, ethylthio, n- or i-propylthio, methylsulphinyl, ethylsulphinyl, methylsulphonyl or ethylsulphonyl, methylaminomethyl, dimethylaminomethyl, vinyl, allyl, 2-methylallyl, propen-1-yl, crotonyl, propargyl, vinyloxy, allyloxy, 2-methylallyloxy, propen-1-yloxy, crotonyloxy, propargyloxy;

trifluoromethyl, trifluoroethyl, difluoromethoxy, trifluoromethoxy, difluorochloromethoxy, trifluoroethoxy, pentafluoroethoxy, 2-chloro-1,1,2-trifluoroethoxy, difluoromethylthio, trifluoromethylthio, difluorochloromethylthio, trifluoromethylsulphinyl or trifluoromethylsulphonyl, methylamino, ethylamino, n- or i-propylamino, dimethylamino, diethylamino, acetyl, propionyl, methoxycarbonyl, ethoxycarbonyl, methylaminocarbonyl, ethylaminocarbonyl, dimethylaminocarbonyl, diethylaminocarbonyl, acryloyl, propioloyl, cyclopentyl, cyclohexyl, propanedlyl, ethyleneoxy, methylenedioxy, ethylenedioxy, each of which is doubly attached and each of which is optionally mono- to tetrasubstituted by identical or different substituents selected from the group consisting of fluorine, chlorine, oxo, methyl or trifluoromethyl or a grouping

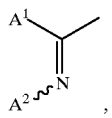

where $A^1$ represents hydrogen or methyl and $A^2$ represents hydroxyl, methoxy, ethoxy, amino, methylamino, methyl, phenyl or benzyl, Q represents oxygen or sulphur, X represents fluorine or chlorine, in particular fluorine, and $L^1$, $L^2$, $L^3$ and $L^4$ are identical or different and, independently of one another, each represents hydrogen, fluorine, chlorine, bromine, cyano, nitro, methyl, ethyl, n- or i-propyl, n-, i-, s- or t-butyl, methoxy, ethoxy, n- or i-propoxy, methylthio, ethylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, preferably represents hydrogen or methyl and in particular represents hydrogen.

The abovementioned general or preferred definitions of a radical apply both to the end products of the formula (I) and also, correspondingly, to the starting materials or intermediates required in each case for the preparation.

Independently of the combination given in each case, the definitions of radicals given in the combinations or preferred combinations of radicals in question specifically for these radicals can also be replaced by definitions of radicals of other preferred ranges.

The formula (II) provides a general definition of the 3-(2-hydroxy-phenyl)-3-methoxyiminomethyl-oxadiazines required as starting materials for carrying out the process a) according to the invention. In this formula (II), $L^1$, $L^2$, $L^3$ and $L^4$ preferably or in particular have those meanings which have already been given, in connection with the description of the compounds of the formula (I) according to the invention, as being preferred or as being particularly preferred for $L^1$, $L^2$, $L^3$ and $L^4$.

The starting materials of the formula (II) are novel and also form part of the subject matter of the present application.

They are obtained (process c) when benzofurandione dioximes of the general formula (VI),

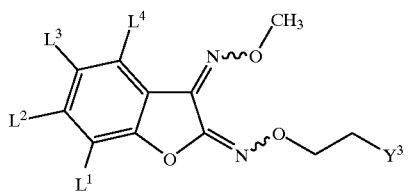

in which $L^1$, $L^2$, $L^3$ and $L^4$ are each as defined above and $Y^3$ represents halogen, alkylsulphonyl or arylsulphonyl are reacted with ammonia, if appropriate in the presence of a diluent and if appropriate under elevated pressure.

The formula (VI) provides a general definition of the benzofurandione dioximes required as starting materials for carrying out the process c) according to the invention. In this formula (VI), $L^1$, $L^2$, $L^3$ and $L^4$ each preferably or in particular have those meanings which have already been mentioned, in connection with the description of the compounds of the formula (I) according to the invention, as being preferred or as being particularly preferred for $L^1$, $L^2$, $L^3$ and $L^4$. $Y^3$ represents halogen, preferably chlorine or bromine, or represents alkylsulphonyl or arylsulphonyl, preferably methylsulphonyl, benzylsulphonyl or tolylsulphonyl.

The starting materials of the formula (VI) are novel and also form part of the subject matter of the present application.

They are obtained when (process d) hydroxyethylbenzofurandione dioximes of the formula (VII)

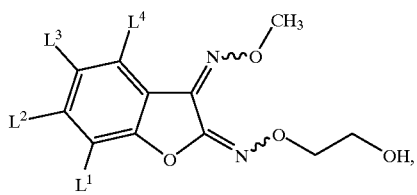

in which $L^1$, $L^2$, $L^3$ and $L^4$ are each as defined above, are reacted with an alkyl- or arylsulphonyl chloride or a halogenating agent, if appropriate in the presence of a diluent and if appropriate in the presence of a base.

The formula (VII) provides a general definition of the hydroxyethylbenzofurandione dioximes required as starting materials for carrying out the process d) according to the invention. In this formula (VII), $L^1$, $L^2$, $L^3$ and $L^4$ each preferably or in particular have those meanings which have already been mentioned, in connection with the description of the compounds of the formula (I) according to the invention, as being preferred or as being particularly preferred for $L^1$, $L^2$, $L^3$ and $L^4$.

The starting materials of the formula (VII) are obtained when, for example, an optionally substituted benzofuranone (X) (cf., for example, Chem. Ber., 30 <1897>, 1081) is initially reacted with methoxyamine to give a benzofuranone oxime (IX) the benzofuranone oxime (IX) is subsequently nitrosated using an alkyl nitrite and the resulting dioxime (VIII) is finally alkylated with, for example, oxirane (see also the Preparation Examples):

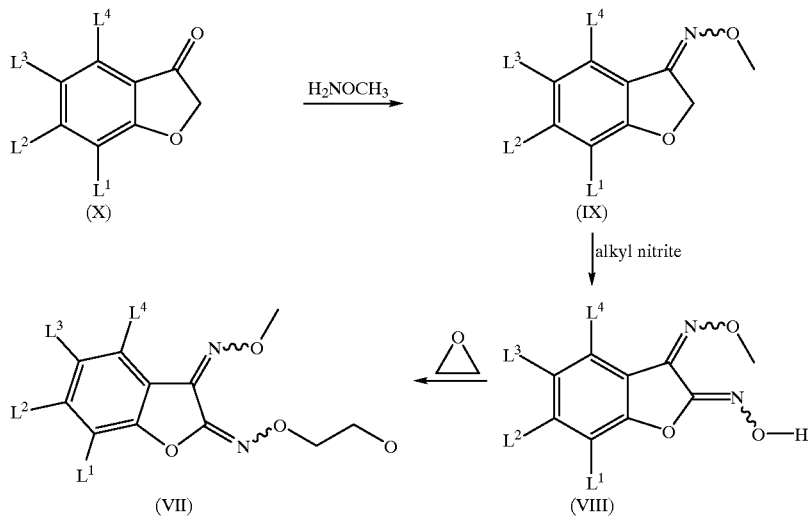

Furthermore, for carrying out the process d) according to the invention, an alkyl- or arylsulphonyl chloride or a halogenating agent is required. Preferred alkyl- or arylsulphonyl chlorides are methyl-, ethyl-, phenyl- or tolylsulphonyl chloride. Suitable halogenating agents are all reagents which are capable of exchanging hydroxyl groups attached to carbon for halogens. Examples include: phosgene, phosphorus trichloride, phosphorus tribromide, phosphorus pentachloride, phosphorus oxychloride, thionyl chloride or thionyl bromide.

The formula (III) provides a general definition of the halogenopyrimidines furthermore required as starting materials for carrying out the process a) according to the invention. In this formula (III), Z, Q and X each preferably or in particular have those meanings which have already been mentioned, in connection with the description of the compounds of the formula (I) according to the invention, as being preferred or as being particularly preferred for Z, Q and X. $Y^1$ represents halogen, preferably fluorine or chlorine.

The starting materials of the formula (III) are known (cf., for example, B. DE-A 4340181; Chem. Ber., 90 <1957>942, 951) and/or they can be prepared by known methods, for example by reacting the trihalogenopyrimidines of the formula (XI) (see below) with ring compounds of the formula (V) (see below).

The formula (IV) provides a general definition of the phenoxypyrimidines required as starting materials for carrying out the process b) according to the invention. In this formula (IV), X, $L^1$, $L^2$, $L^3$ and $L^4$ each preferably or in particular have those meanings which have already been mentioned, in connection with the description of the compounds of the formula (I) according to the invention, as being preferred or as being particularly preferred for X, $L^1$, $L^2$, $L^3$ and $L^4$. $Y^2$ represents halogen, preferably fluorine or chlorine.

The starting materials of the formula (IV) are novel and also form part of the subject matter of the present application.

The phenoxypyrimidines of the general formula (IV) are obtained (process e), when 3-(2-hydroxy-phenyl)-3-methoxyiminomethyl-oxadiazines of the formula (II) are reacted with a trihalogenopyrimidine of the general formula (XI)

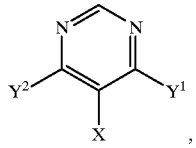

(XI)

in which
X, $Y^1$ and $Y^2$ are identical or different and each represents halogen,
if appropriate in the presence of a diluent, if appropriate in the presence of an acid acceptor and if appropriate in the presence of a catalyst.

The 3-(2-hydroxy-phenyl)-3-methoxyiminomethyl-oxadiazines of the formula (II) required as starting materials for carrying out the process e) according to the invention have already been described in connection with the description of the process a) according to the invention.

The formula (XI) provides a general definition of the trihalogenopyrimidines furthermore required as starting materials for carrying out the process e) according to the invention. In this formula (XI) X, $Y^1$ and $Y^2$ each represent halogen, preferably fluorine or chlorine.

The trihalogenopyrimidines of the formula (XI) are known and/or can be prepared by known methods (cf. for example, Chesterfield et al., J. Chem. Soc., 1955; 3478, 3480).

The formula (V) provides a general definition of the ring compounds furthermore required as starting materials for carrying out the process b) according to the invention. In this formula (V), Z and Q each preferably or in particular have those meanings which have already been mentioned, in connection with the description of the compounds of the formula (I) according to the invention, as being preferred or as being particularly preferred for Z and Q.

The ring compounds of the formula (V) are known chemicals for synthesis or can be prepared by known methods.

Suitable diluents for carrying out the processes a), b) and e) according to the invention are all inert organic solvents. These preferably includes ethers, such as diethyl ether, diusopropyl ether, methyl t-butyl ether, methyl t-amyl ether, dioxane, tetrahydrofuran, 1,2-dimethoxyethane, 1,2-diethoxyethane or anisole; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; sulphoxides, such as dimethyl sulphoxide; or sulphones, such as sulpholane.

Suitable diluents for carrying out the process c) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; ethers, such as diethyl ether, diusopropyl ether, methyl t-butyl ether, methyl t-amyl ether, dioxane, tetrahydrofuran, 1,2-dimethoxyethane, 1,2-diethoxyethane or anisole; amides, such as N,N-dimethylformamide, N,N-dimethylacetamide, N-methylformanilide, N-methylpyrrolidone or hexamethylphosphoric triamide; sulphoxides, such as dimethyl sulphoxide; sulphones, such as sulpholane; alcohols, such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether, mixtures thereof with water or pure water.

Suitable diluents for carrying out the process d) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters such as methyl acetate or ethyl acetate; sulphoxides, such as dimethyl sulphoxide, sulphones, such as sulpholane.

If appropriate the processes a), b) and e) according to the invention are carried out in the presence of a suitable acid acceptor. Suitable acid acceptors are all customary inorganic or organic bases. These preferably include alkaline earth metal or alkali metal hydrides, hydroxides, alkoxides, carbonates or bicarbonates, such as, for example, sodium hydride, sodium amide, potassium tert-butoxide, sodium hydroxide, potassium hydroxide, sodium carbonate, potassium carbonate, potassium bicarbonate or sodium bicarbonate.

If appropriate, the process d) according to the invention is carried out in the presence of a suitable acid acceptor. Suitable acid acceptors are all customary inorganic or organic bases. These preferably include alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, and also tertiary amines, such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU).

Suitable catalysts for the processes a), b) and e) according to the invention are all copper(I) salts, such as, for example, copper(I) chloride, copper(I) bromide or copper(I) iodide.

When carrying out the processes a), b) and e) according to the invention, the reaction temperatures can be varied within a relatively wide range. In general, the reactions are carried out at temperatures from −20° C. to 100° C., preferably at temperatures from −10° C. to 80° C.

When carrying out the process c) according to the invention, the reaction temperatures can be varied within a relatively wide range. In general, the reaction is carried out at temperatures from 20° C. to 250° C., preferably at temperatures from 50° C. to 150° C.

When carrying out the process d) according to the invention, the reaction temperatures can be varied within a relatively wide range. In general, the reaction is carried out at temperatures from −20° C. to 80° C., preferably at temperatures from −10° C. to 40° C.

For carrying out the process a) according to the invention for preparing the compounds of the formula (I), generally 0.5 to 15 mol, preferably 0.8 to 8 mol, of substituted halogenopyrimidine of the formula (III) are employed per mole of the 3-(2-hydroxy-phenyl)-3-methoxyiminomethyl-oxadiazine of the formula (II).

For carrying out the process b) according to the invention for preparing the compounds of the formula (I), generally 0.5 to 15 mol, preferably 0.8 to 8 mol, of the ring compound of the general formula (V) are employed per mole of the phenoxypyrimidine of the formula (IV).

For carrying out the process d) according to the invention for preparing the compounds of the formula (VI), generally 1 to 15 mol, preferably 2 to 8 mol, of alkyl- or arylsulphonyl chloride, or of halogenating agent, are employed per mole of hydroxyethylbenzofurandione dioxime of the formula (VII).

For carrying out the process e) according to the invention for preparing the compounds of the formula (IV), generally 1 to 15 mol, preferably 2 to 8 mol of a trihalogenopyrimidine of the general formula (XI) are employed per mole of the 3-(2-hydroxy-phenyl)-3-methoxyiminomethyl-oxadiazine of the formula (II).

The processes a), b), d) and e) are generally carried out under atmospheric pressure. However, it is also possible to operate under elevated or reduced pressure—generally between 0.1 bar and 10 bar.

The process c) according to the invention is generally carried out under elevated pressure. The process is preferably carried out at a pressure between 2 and 100 bar, in particular between 3 and 50 bar.

Generally customary processes are employed for carrying out the reactions, for workup and for isolation of the reaction products (cf. also the Preparation Examples).

The compounds according to the invention have potent microbicidal activity and can be employed for controlling undesirable microorganisms, such as fungi and bacteria, in crop protection and in the protection of materials.

Fungicides are employed in crop protection for controlling Plasmodiophoromycetes, Oomycetes, Chytridiomycetes, Zygomycetes, Ascomycetes, Basidiomycetes and Deuteromycetes.

Bactericides are employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above are mentioned as examples, but not by way of limitation:

Xanthomonas species, such as, for example, *Xanthomonas campestris* pv. *oryzae*;
Pseudomonas species, such as, for example, *Pseudomonas syringae* pv. *lachrymans*;
Erwinia species, such as, for example, *Erwinia amylovora*;
Pythium species, such as, for example, *Pythium ultimum*;
Phytophthora species, such as, for example, *Phytophthora infestans*;
Pseudoperonospora species, such as, for example, *Pseudoperonospora humuli* or *Pseudoperonospora cubensis*;
Plasmopara species, such as, for example, *Plasmopara viticola*;
Bremia species, such as, for example, *Bremia lactucae*,
Peronospora species, such as, for example, *Peronospora pisi* or *P. brassicae*;
Erysiphe species, such as, for example, *Erysiphe graminis*;
Sphaerotheca species, such as, for example, *Sphaerotheca fuliginea*;
Podosphaera species, such as, for example, *Podosphaera leucotricha*;
Venturia species, such as, for example, *Venturia inaequalis*;
Pyrenophora species, such as, for example, *Pyrenophora teres* or *P. graminea*
(conidia form: Drechslera, syn: Helminthosporium);
Cochliobolus species, such as, for example, *Cochliobolus sativus*
(conidia form: Drechslera, syn: Helminthosporium);
Uromyces species, such as, for example, *Uromyces appendiculatus*;
Puccinia species, such as, for example, *Puccinia recondita*;
Sclerotinia species, such as, for example, *Sclerotinia sclerotiorum*
Tilletia species, such as, for example, *Tilletia caries*;
Ustilago species, such as, for example, *Ustilago nuda* or *Ustilago avenae*;
Pellicularia species, such as, for example, *Pellicularia sasakii*;
Pyricularia species, such as, for example, *Pyricularia oryzae*;
Fusarium species, such as, for example, *Fusarium culmorum*;
Botrytis species, such as, for example, *Botrytis cinerea*;
Septoria species, such as, for example, *Septoria nodorum*;
Leptosphaeria species, such as, for example, *Leptosphaeria nodorum*;
Cercospora species, such as, for example, *Cercospora canescens*;
Alternaria species, such as, for example, *Alternaria brassicae*; and
Pseudocercosporella species, such as, for example, *Pseudocercosporella herpotrichoides*.

The fact that the active compounds are well tolerated by plants at the concentrations required for controlling plant diseases permits the treatment of aerial parts of plants, of propagation stock and seeds, and of the soil.

The active compounds according to the invention can be employed particularly successfully for controlling cereal diseases, such as, for example, against Leptosphaeria, Puccinia or Fusarium species, for controlling diseases in fruit and vegetable growing and viticulture, such as, for example, against Venturia, Sphaerotheca or Plasmopora species, for controlling rice diseases, such as, for example, against Pyricularia species.

Furthermore, the compounds according to the invention may also be employed to increase the yield of crops. They also have reduced toxicity and are tolerated well by plants.

Depending on their particular physical and/or chemical properties, the active compounds can be converted to the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. If the extender used is water, it is also possible to use for example organic solvents as auxiliary solvents. Suitable liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as highly disperse silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

The active compounds according to the invention can be used as such or in their formulations also mixed with known fungicides, bactericides, acaricides, nematicides or insecticides in order thus, for example, to widen the spectrum of action or to prevent development of resistance. In many cases, synergistic effects are achieved, i.e. the activity of the mixture exceeds the activity of the individual components.

Examples of co-components in mixtures are the following compounds:

Fungicides:

aldimorph, ampropylfos, ampropylfos potassium, andoprim, anilazine, azaconazole, azoxystrobin, benalaxyl, benodanil, benomyl, benzamacril, benzamacril-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuiram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulphamide, flutolanil, flutriafol, folpet, fosetyl-aluminium, fosetyl-sodium, fthalide, fuberidazole, furalaxyl, furametpyr, furcarbonil, furconazole, furconazolecis, furmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulphocarb, methfuroxam, metiram, metomeclam, metsulphovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur, quinconazole, quintozene(PCNB), sulphur and sulphur preparations, tebuconazole, tecloftalam, tecnazene, tetcyclasis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole, uniconazole, validamycin A, vinclozolin, viniconazole, zarilamide, zineb, ziram and also Dagger G,

OK-8705,

OK-8801,

α-(1,1-dimethylethyl)-β-(2-phenoxyethyl)-1H-1,2,4-triazole-1-ethanol,

α-(2,4-dichlorophenyl)-β-fluoro-b-propyl-1H-1,2,4-triazole-1-ethanol,

α-(2,4-dichlorophenyl)-β-methoxy-a-methyl-1H-1,2,4-triazole-1-ethanol,

α-(5-methyl-1,3-dioxan-5-yl)-β-[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-a-(methoxyimino)-N-methyl-2-phenoxy-phenylacetamide, 1-isopropyl {2-methyl-1-[[[1-(4-methylphenyl)-ethyl]-amino]-carbonyl]-propyl}-carbamate, 1-(2,4-dichlorophenyl)-2-(1H-1,2,4-triazol-1-yl)-ethanone-O-(phenylmethyl)-oxime, 1-(2-methyl-1-naphthalenyl)-1H-pyrrol-2,5-dione, 1-(3,5-dichlorophenyl)-3-(2-propenyl)-2,5-pyrrolidinedione, 1-[(diiodomethyl)-sulphonyl]-4-methyl-benzene, 1-[[2-(2,4-dichlorophenyl)-1,3-dioxolan-2-yl]-methyl]-1H-imidazole, 1-[[2-(4-chlorophenyl)-3-phenyloxiranyl]-methyl]-1H-1,2,4-triazole, 1-[1-[2-[(2,4-dichlorophenyl)-methoxy]-phenyl]-ethenyl]-1H-imidazole, 1-methyl-5-nonyl-2-(phenylmethyl)-3-pyrrolidinole, 2',6'-dibromo-2-methyl-4'-trifluoromethoxy-4'-trifluoro-methyl-1,3-thiazole-5-carboxanilide, 2,2-dichloro-N-[1-(4-chlorophenyl)-ethyl]-1-ethyl-3-methyl-cyclopropanecarboxamide, 2,6-dichloro-5-(methylthio)-4-pyrimidinyl-thiocyanate, 2,6-dichloro-N-(4-trifluoromethylbenzyl)-benzamide, 2,6-dichloro-N-[[4-(trifluoromethyl)-phenyl]-methyl]-benzamide, 2-(2,3,3-triiodo-2-propenyl)-2H-tetrazole, 2-[(1-methylethyl)-sulphonyl]-5-(trichloromethyl)-1,3,4-thiadiazole, 2-[[6-deoxy-4-O-(4-O-methyl-β-D-glycopyranosyl)-a-D-glucopyranosyl]-amino]-4-methoxy-1H-pyrrolo[2,3-d]pyrimidine-5-carbonitrile, 2-aminobutane, 2-bromo-2-(bromomethyl)-pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)-acetamide, 2-phenylphenol (OPP), 3,4-dichloro-1-[4-(difluoromethoxy)-phenyl]-1H-pyrrol-2,5-dione, 3,5-dichloro-N-[cyano-[(1-methyl-2-propynyl)-oxy]-methyl]-benzamide, 3-(1,1-dimethylpropyl-1-oxo-1H-indene-2-carbonitrile, 3-[2-(4-chlorophenyl)-5-ethoxy-3-isoxazolidinyl]-pyridine, 4-chloro-2-cyano-N,N-dimethyl-5-(4-methylphenyl)-1H-imidazole-1-sulphonamide, 4-methyl-tetrazolo[1,5-a]quinazolin-5(4H)-one, 8-(1,1-dimethylethyl)-N-ethyl-N-propyl-1,4-dioxaspiro[4.5]decane-2-methaneamine, 8-hydroxyquinoline sulphate, 9H-xanthene-2-[(phenylamino)-carbonyl]-9-carboxylic hydrazide, bis-(1-methylethyl)-3-methyl-4-[(3-methylbenzoyl)-oxy]-2,5-thophenedicarboxylate, cis-1-(4-chlorophenyl)-2-(1H-1,2,4-triazol-1-yl)-cycloheptanol, cis-4-[3-[4-(1,1-dimethylpropyl)-phenyl-2-methylpropyl]-2,6-dimethyl-morpholinehydrochloride, ethyl [(4-chlorophenyl)-azo]-cyanoacetate, potassium hydrogen carbonate, methanetetrathiol sodium salt, methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methyl-cyclohexanecarboxamide,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulphonamide,
N-(4-cyclohexylphenyl)-1,4,5,6-tetrahydro-2-pynmidineamine,
N-(4-hexylphenyl)-1,4,5,6-tetrahydro-2-pyrimidineamine,
N-(5-chloro-2-methylphenyl)-2-methoxy-N-(2-oxo-3-oxazolidinyl)-acetamide,
N-(6-methoxy)-3-pyridinyl)-cyclopropanecarboxamide,
N-[2,2,2-trichloro-1-[(chloroacetyl)-amino]-ethyl]-benzamide,
N-[3-chloro-4,5-bis(2-propinyloxy)-phenyl]-N'-methoxy-methanimidamide,
N-formyl-N-hydroxy-DL-alanine-sodium salt,
O,O-diethyl[2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyrane-2,1'(3'H)-isobenzofuran]-3'-one,
Bactericides:
bromopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.
Insecticides/acaricides/nematicides:
abamectin, acephate, acrinathrin, alanycarb, aldicarb, alphamethrin, amitraz, avermectin, AZ 60541, azadirachtin, azinphos A, azinphos M, azocyclotin,
*Bacillus thuringiensis*, 4-bromo-2-(4-chlorophenyl)-1-(ethoxymethyl)-5-(tri-fluoromethyl)-1H-pyrrole-3-carbonitrile, bendiocarb, benfuracarb, bensultap, betacyfluthrin, bifenthrin, BPMC, brofenprox, bromophos A, bufencarb, buprofezin, butocarboxin, butylpyridaben,
cadusafos, carbaryl, carbofuran, carbophenothion, carbosulphan, cartap, chloethocarb, chlorethoxyfos, chlorfenapyr, chlorfenvinphos, chlorfluazuron, chlormephos, N-[(6-chloro-3-pyridinyl)-methyl]-N'-cyano-N-methyl-ethaneimidamide, chlorpyrifos, chlorpyrifos M, cis-resmethrin, clocythrin, clofentezine, cyanophos, cyclopothrin, cyfluthrin, cyhalothrin, cyhexatin, cypermethrin, cyromazine,
deltamethrin, demeton M, demeton S, demeton s-methyl, diafenthiruon, diazinon, dichlofenthion, dichlorvos, dicliphos, dicrotophos, diethion, diflubenzuron, dimethoate, dimethylvinphos, dioxathion, disulphoton,
edifenphos, emamectin, esfenvalerate, ethiofencarb, ethion, ethofenprox, ethoprophos, etrimphos,
fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, fluazuron, flucycloxuron, flucythrinate, flufenoxuron, flufenprox, fluvalinate, fonophos, formothion, fosthiazate, fubfenprox, furathiocarb,
HCH, heptenophos, hexaflumuron, hexythiazox,
imidacloprid, iprobenfos, isazophos, isofenphos, isoprocarb, isoxathion, ivermectin,
lambda-cyhalothrin, lufenuron,
malathion, mecarbam, mervinphos, mesulphenphos, metaldehyde, methacrifos, methamidophos, methidathion, methiocarb, methomyl, metolcarb, milbemectin, monocrotophos, moxidectin,
naled, NC 184, nitenpyram,
omethoate, oxamyl, oxydemethon M, oxydeprofos,
parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pyrimidifen, pyriproxifen,
quinalphos,
salithion, sebufos, silafluofen, sulphotep, sulprofos,
tebufenozide, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb,
vamidothion, XMC, xylylcarb, zetamethrin.

It is also possible to admix other known active compounds, such as herbicides, fertilizers and growth-promoting substances.

The active compounds can be used as such or in the form of their formulations or the use forms prepared therefrom, such as ready-to-use solutions. suspensions, wettable powders, pastes, soluble powders, dusts and granules. They are used in the customary manner, for example by pouring, spraying, atomizing, spreading, foaming, brushing on and the like. It is further possible to apply the active compounds by the ultra-low volume method or to inject the active compound formulation, or the active compound itself, into the soil. The seed of the plants can also be treated.

When the active compounds according to the invention are employed as fungicides, the application rates can be varied within a relatively wide range, depending on the form of application. In the treatment of parts of plants, the active compound concentrations in the use forms are, in general, between 0.1 and 10,000 g/ha, preferably between 10 and 1000 g/ha. In the treatment of seed, amounts of active compound of from 0.001 to 50 g, preferably 0.01 to 10 g, are generally required per kilogram of seed. In the treatment of the soil, active compound concentrations of between 0.1 and 10,000 g/ha, preferably between 1 and 5000 g/ha, are employed.

PREPARATION EXAMPLES

Example 1

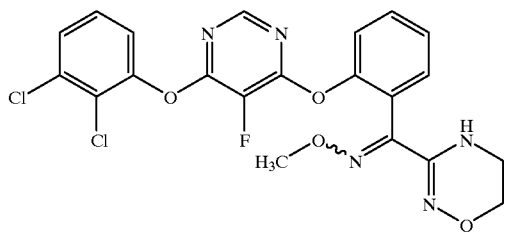

Process b

At 20° C., initially 0.33 g (2 mmol) of 2,3-dichlorophenol and subsequently 0.33 g (2,4 mmol) of potassium carbonate are added to a solution of 0.7 g (2 mmol) of 3-{1-[2-(4,5- difluoropyrimid-6-yloxy)-phenyl]-1-(methoximino)-methyl}-5,6-dihydro-4H-1,2,4-oxadiazine in 30 ml of acetonitrile. The mixture is stirred overnight, filtered off, taken up in 150 ml of ethyl acetate and washed with water. Finally, the organic phase is dried over sodium sulphate and concentrated under reduced pressure, leaving a viscous oil which slowly crystallizes. This gives 0.9 g (91.8% of theory) of 3-{1-[2-(4-<2,3-dichlorophenoxy>-5-fluoropyrimid-6-yloxy)-phenyl]-1-(methoximino)-methyl}-5,6-dihydro-4H-1,2,4-oxadiazine.

HPLC: logP: 3.45.

By the method of Example (1), and according to the general description of the preparation processes a) and b) according to the invention, the compounds of the formula (I-a) listed in Table 1 below are likewise obtained:

TABLE 1

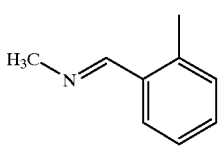

(I-a)

| Example | Q | Z | logP* |
|---|---|---|---|
| 2 | O | 3-chloro-2-methylphenyl | 3.52 |
| 3 | O | 2-chlorophenyl | 3.02 |
| 4 | O | 2,3-dimethylphenyl | 3.29 |
| 5 | O | 3-chlorophenyl | 3.23 |
| 6 | O | 4-chlorophenyl | 3.23 |
| 7 | O | 2-ethenylphenyl | 3.38 |
| 8 | O | 2-tolyl | 3.01 |
| 9 | O | 2-bromophenyl | 3.08 |
| 10 | O | 2-fluorophenyl | 2.85 |
| 11 | O | 2-ethylphenyl | 3.32 |
| 12 | O | 3-(t-butyl)phenyl | 3.96 |
| 13 | O | 2-(i-propyl)phenyl | 3.59 |
| 14 | O | 2-methoxyphenyl | 2.70 |
| 15 | O | 2,4-dimethylphenyl | 3.38 |
| 16 | O | 2,5-dimethylphenyl | 3.35 |
| 17 | O | 2-cyclopentylphenyl | 4.01 |
| 18 | O | 2-chloro-5-methylphenyl | 3.35 |
| 19 | O | 2,6-dimethylphenyl | 3.29 |
| 20 | O | 3-tolyl | 3.10 |
| 21 | O | 4-tolyl | 3.08 |
| 22 | O | 2-(t-butyl)phenyl | 3.84 |
| 23 | O | 3-methoxyphenyl | 2.80 |
| 24 | O | 3-trifluoromethylphenyl | 3.39 |
| 25 | O | 4-trifluoromethoxyphenyl | 3.54 |
| 26 | O | 2-chloro-4-trifluoromethylphenyl | 3.76 |
| 27 | O | 2-chloro-4-trifluoromethoxyphenyl | 3.86 |
| 28 | O | 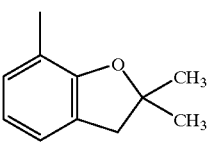 | |
| 29 | O | 2-cyanophenyl | 2.56 |
| 30 | O | 2-methyl-4-trifluoromethoxyphenyl | 3.80 |
| 31 | O | 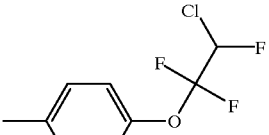 | 3.30 |
| 32 | O | 4-trifluoromethylthiophenyl | 3.84 |
| 33 | O | 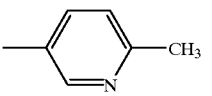 | 3.56 |
| 34 | O | phenyl | 2.76 |
| 35 | O | 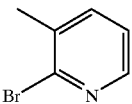 | 1.58 |
| 36 | O | 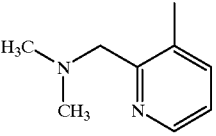 | 2.43 |
| 37 | O | 3-pyridyl | 1.73 |
| 38 | O | 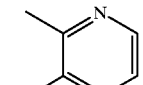 | |
| 39 | O | 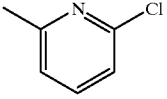 | |
| 40 | O | 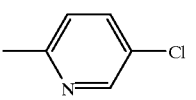 | 2.62 |
| 41 | O | (5-chloro-2-pyridyl) | 2.65 |

TABLE 1-continued

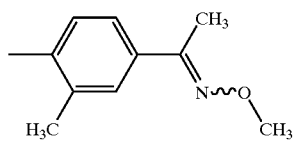

(I-a)

| Example | Q | Z | logP* |
|---|---|---|---|
| 42 | O | 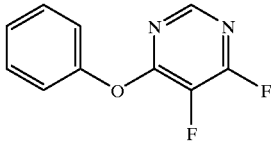 | 3.56 |
| 43 | O | benzyl | |
| 44 | O | 3-methylbenzyl | |
| 45 | O | 2-chlorobenzyl | 2.8 |
| 46 | O | 3-chlorobenzyl | 3.44 |
| 47 | O | 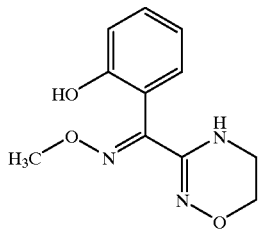 | |
| 48 | S | phenyl | 3.07/3.10 |
| 49 | S | 4-bromophenyl | 3.69 |
| 50 | S | 4-chlorophenyl | 3.57 |
| 51 | S | 4-tolyl | 3.45 |
| 52 | S | 3-bromophenyl | 3.66 |
| 53 | S | 3-chlorophenyl | 3.56 |
| 54 | S | 2-chlorophenyl | |
| 55 | S | 2,4-dichloro-3-trifluoromethylphenyl | 4.30 |
| 56 | S | 4-chloro-3-trifluoromethylphenyl | |
| 57 | S | cyclohexyl | 4.01 |
| 58 | S | benzyl | 3.42 |
| 59 | O | 2-chloro-3-methylphenyl | 3.34 |
| 60 | O | 2-ethylthiomethylphenyl | 3.40 |
| 61 | O | 2-methoxymethylphenyl | 2.74 |
| 62 | O | 2-ethoxymethylphenyl | 3.04 |
| 63 | O | 2-methylthiophenyl | 2.95 |
| 64 | O | 2-ethylthiophenyl | 3.26 |

*The logP values were determined in accordance with EEC Directive 79/831 Annex V. A8 by HPLC (gradient method, acetonitrile/0.1% aqueous phosphoric acid)

PREPARATION OF THE STARTING MATERIALS OF THE FORMULA (II)

Example (II-1):

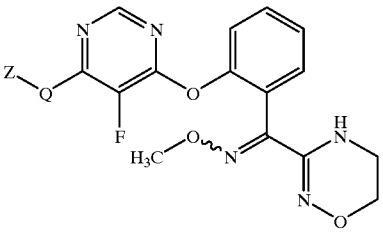

Process c)

1.26 g (4 mmol) of benzofuran-2,3-dione 2-[O-(2-methylsulphonyloxy-ethyl)-oxime] 3-(O-methyl-oxime) are initially charged in 15 ml of methanol in an autoclave. 2.5 g (147 mmol) of ammonia are then condensed in, and the autoclave is heated under autogenous pressure at 100° C. for 16 hours. The autoclave is cooled to 20° C., the reaction mixture is removed and the solvent is distilled off under reduced pressure. Finally, the residue is stirred with water, and the resulting white solid is filtered off and dried in a drying cabinet overnight. This gives 0.9 g (96% of theory) of 3-{1-[2-hydroxyphenyl]-1-(methoximino)-methyl}-5,6-dihydro-4H-1,2,4-oxadiazine.

$^1$H NMR: δ=3.57 (m, 2H); 3.98 (s, 3H); 4.05 (m, 2H) ppm

PREPARATION OF THE STARTING MATERIALS OF THE FORMULA (III)

Example (III-1)

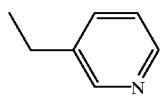

At 0° C., a solution of 42.4 g (0.45 mol) of phenol and 50.4 g (0.45 mol) of potassium t-butoxide in 400 ml of tetrahydrofuran are added dropwise to a solution of 80 g (0.6 mol) of 4,5,6-trifluoropyrimidine in 1 l of tetrahydrofuran. After the addition is completed, the reaction mixture is stirred at 0° C. for 30 minutes and then poured into water and extracted with ethyl acetate. The organic phase is dried over sodium sulphate and concentrated under reduced pressure, and the residue is stirred with low-boiling petroleum ether. This gives 63.8 g (68.1% of theory) of 4-phenoxy-5,6-difluoropyrimidine of melting point 65–66° C.

Preparation of the precursor:

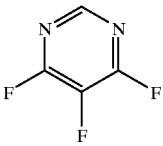

A mixture of 609 g of potassium fluoride in 2.3 l of sulpholan is dried by distilling off 500 ml of liquid at 145° C. and 20 mbar. 1054 g of 5-chloro-4,6-difluoropyrimidine (DE-A 3843558) and 25 g of tetraphenylphosphonium bromide are added, a nitrogen pressure of 5 bar is applied and the mixture is stirred at 240° C. for 24 hours, in the course of which the pressure increases to 11 bar. The reaction mixture is cooled to 80° C. and vented. The mixture is then slowly heated at atmospheric pressure, and the product is distilled off. Once the bottom temperature has reached 200° C., the pressure is lowered to 150 mbar to accelerate the distillation and to obtain further product. This gives a total of 664 g (70.7% of theory) of 4,5,6-trifluoropyrimidine of boiling point 86 to 87° C.

PREPARATION OF THE STARTING MATERIALS OF THE FORMULA (IV)

Example (IV-1):

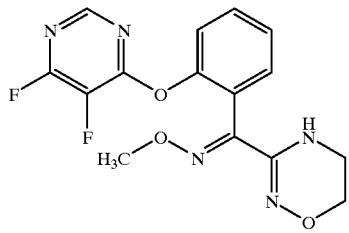

Process e)

At 20° C., initially 0.7 g (5.1 mmol) of 4,5,6-trifluoropyrimidine and subsequently 1.4 g (10.2 mmol) of potassium carbonate are added to a solution of 1.2 g (5.1 mmol) of 3-{1-[2-hydroxyphenyl]-1-(methoximino)-methyl}-5,6-dihydro-4H-1,2,4-oxa-diazine in 30 ml of acetonitrile. The mixture is stirred overnight, filtered off, taken up in 150 ml of ethyl acetate and washed with water. Finally, the organic phase is dried over sodium sulphate and concentrated under reduced pressure, giving a viscous oil which slowly crystallizes. This gives 1.4 g (82% of theory) of 3-{1-[2-(4,5-difluoropyrimid-6-yloxy)-phenyl]-1-(methoximino)-methyl }-5,6-dihydro-4H-1,2,4-oxadiazine.

HPLC: logP: 1.97

PREPARATION OF THE STARTING MATERIALS OF THE FORMULA (VI)

Example (VI-1):

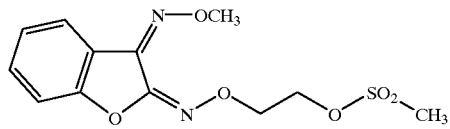

At 20° C., 3.2 g (0.0135 mol) of benzofuran-2,3-dione 2-[O-(2-hydroxy-ethyl)-oxime] 3-(O-methyl-oxime) are initially in 100 ml of methylene chloride and mixed with 1.05 ml (0.0135 mol) of methanesulphonyl chloride. After 15 minutes, 5.6 ml (0.0406 mol) of triethylamine are added to this mixture at 10° C. and with ice-cooling. Finally, the mixture is warmed to 20° C. and stirred for another 4.5 hours. The reaction mixture is then taken in methyl t-butyl ether, washed with water, dried over magnesium sulphate and concentrated under reduced pressure. This gives 4.0 g (94.2% of theory) of benzofuran-2,3-dione 2-[O-(2-methylsulphonyloxy-ethyl)-oxime]3-(O-methyl-oxime) as a white solid.

HPLC: logP: 2.39

PREPARATION OF PRECURSORS OF FORMULAE (VII), (VIII) and (IX)

Compound (IX-1)

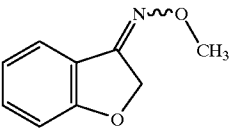

6.7 g (0.05 mol) of benzofuran-3-one, 4.2 g (0.05 mol) of O-methylhydroxylamine hydrochloride and 4.1 g (0.05 mol) of sodium acetate in 50 ml of methanol are heated under reflux for 3 hours. The solvent is distilled off under reduced pressure and the reaction mixture is poured into water and extracted with ethyl acetate. The organic phase is washed with saturated aqueous sodium carbonate solution. The organic phase is dried over sodium sulphate and the solvent is distilled off under reduced pressure. This gives 7.27 g (89.2% of theory) of crude benzofuran-3-one O-methyl-oxime. For analysis, this product is subjected to kugelrohr distillation at 2 torr and 70° C. This gives an oil which both according to NMR analysis and according to HPLC analysis comprises two stereoisomers (79% of isomer B and 21% of isomer A).

$^1$H NMR spectrum (DMSO-$d_6$/TMS): δ=3.93 (3H, isomer B); 3.93 (3H, isomer A); 5.11 (2H, isomer A); 5.16 (2H, isomer B); 7.0–7.07 (2H); 7.39–7.45 (1H); 7.54/7.57 (1H, isomer B); 7.95–8.02 (1H, isomer A) ppm.

Compound (VIII-1)

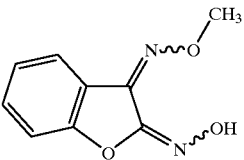

3.92 g (0.035 mol) of potassium tert-butoxide are dissolved in 40 ml of tert-butanol. This solution is admixed with a solution of 5.7 g (0.035 mol) of benzofuran-3-one O-methyl-oxime and 7.2 g (0.07 mol) of tert-butyl nitrite in 10 ml tert-butanol. The mixture is stirred without cooling for two hours and then admixed with 20 ml of 2N aqueous hydrochloric acid. The product that crystallizes out is filtered off, washed repeatedly with water and dried in a desiccator. This gives 3.19 g (47.1% of theory) of benzofuran-2,3-dione 3-(O-methyl-oxime) 2-oxime as a mixture of two stereoisomers comprising 86.33% of isomer A and 12.98% of isomer B (HPLC).

$^1$H NMR spectrum (DMSO-$d_6$/TMS): δ=4.10 (3H, isomer B); 4.11 (3H; isomer A); 7.21/7.24/7.26 (1H); 7.31/7.34 (1H); 7.51/7.53/7.56 (1H); 7.63/7.65 (1H, isomer B); 8.02/8.05 (1H, isomer A); 11.36 (1H, isomer A); 11.75 (1H, isomer B) ppm.

Compound (VII-1)

Process b)

At 20° C., 264.3 g (6.0 mol) of ethylene oxide are introduced over a period of 85 minutes into a solution of 192.2 g (1.0 mol) of benzofuran-2,3-dione 3-(O-methyl-oxime) 2-oxime in 2 l of water. The solution is cooled to 5° C. and 70 g (1.06 mol) of potassium hydroxide pellets are added, the temperature rising to 10° C. in the course of the addition. Stirring without any further cooling is continued for 165 minutes and the resulting precipitate is filtered off with suction, washed with portions of 500 ml of ice-water and dried at 40° C. in a vacuum drying cabinet. This gives 143.0 g (61% of theory) of benzofuran-2,3-dione 2-[O-(2-hydroxy-ethyl)-oxime] 3-(O-methyl-oxime) as a mixture of two stereoisomers.

HPLC: logP=1.65 (0.5%); 1.79 (99.5%)

USE EXAMPLES

Example A

*Leptosphaeria nodorum* test (wheat)/protective

Solvent: 25 parts by weight of N,N-dimethylacetamide

Emulsifier: 0.6 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are sprayed with a spore suspension of *Leptosphaeria nodorum*. The plants remain in an incubation cabin at 20° C. and 100% relativer atmospheric humidity for 48 hours.

The plants are place in a greenhouse at a temperature of approximately 15° C. and a relative atmospheric humidity of 80%.

Evaluation is carried out 10 days after the inoculation. 0% means an efficacy which corresponds to that of the control, while an efficacy of 100% means that no infection is observed.

In this test, the substance according to the invention mentioned in Example (3) shows, at an application rate of 250 g/ha, an efficacy of 90% or more.

TABLE A

*Leptosphaeria nodorum* test (wheat)/protective

| Active compound | Application rate of active compound in g/ha | Efficacy in % |
|---|---|---|
| according to the invention | | |
| (3) | 250 | 100 |

Example B

Puccinia test (wheat)/curative

Solvent: 25 parts by weight of N,N-dimethylacetamide

Emulsifier: 0.6 parts by weight of alkylaryl polyglycol ether

To prepare a suitable preparation of active compound, 1 part by weight of active compound is mixed with the stated amounts of solvent and emulsifier, and the concentrate is diluted with water to the desired concentration.

To test for curative activity, young plants are sprayed with a conidia suspension of *Puccinia recondita*. The plants remain in an incubation cabin at 20° C. and 100% relative atmospheric humidity for 48 hours. The plants are subsequently sprayed with the preparation of active compound in the stated application rate.

The plants are placed in a greenhouse at a temperature of approximately 20° C. and a relative atmospheric humidity of approximately 80% to promote the development of rust pustules.

Evaluation is carried out 10 days after the inoculation. 0% means an efficacy which corresponds to that of the control, while an efficacy of 100% means that no infection is observed.

In this test, the substance according to the invention mentioned in Example (3) shows, at an application rate of 250 g/ha, an efficacy of 90% or more.

TABLE B

Puccinia test (wheat)/curative

| Active compound | Application rate of active compound in g/ha | Efficacy in % |
|---|---|---|
| according to the invention | | |
| (3) [structure: 2-chlorophenoxy-pyrimidine with fluoro, methoxyimino, and oxazine moiety] | 250 | 100 |

Example C
*Fusarium nivale* (var. *nivale*) test (wheat)/protective

Solvent: 25 parts by weight of N,N-dimethylacetamide
Emulsifier: 0.6 parts by weight of alkylaryl polyglycol ether To prepare a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are sprayed with a conidia suspension of *Fusarium nivale* (var. *nivale*).

The plants are placed in a greenhouse under transparent incubation hoods at a temperature of approximately 15° C. and a relative atmospheric humidity of approximately 100%.

Evaluation is carried out 4 days after the inoculation. 0% means an efficacy which corresponds to that of the control, while an efficacy of 100% means that no infection is observed.

In this test, the substances according to the invention mentioned in Examples (1) and (2) show, at an application rate of 250 g/ha, an efficacy of 90% or more.

TABLE C

*Fusarium nivale* (var. nivale) test (wheat)/protective

| Active compound | Application rate of active compound in g/ha | Efficacy in % |
|---|---|---|
| according to the invention | | |
| (2) [structure: 2,3-dichlorophenoxy-pyrimidine with fluoro, methoxyimino, and oxazine moiety] | 250 | 100 |
| (1) [structure: 2,3-dichlorophenoxy-pyrimidine with fluoro, methoxyimino, and oxazine moiety] | 250 | 100 |

Example D
Plasmopara test (grapevine)/protective

Solvent: 47 parts by weight of acetone

Emulsifier: 3 parts by weight of alkylaryl polyglycol ether

To prepare a suitable preparation of active compound, 1 part by weight of active compounds is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of *Plasmopara viticola* and then remain in an incubation cabin at approximately 20° C. and 100% relative atmospheric humidity for 1 day. The plants are subsequently placed in a greenhouse at approximately 21° C. and approximately 90% relative atmospheric humidity for 5 days. The plants are then moistened and placed in an incubation cabin for 1 day.

Evaluation is carried out 6 days after the inoculation. 0% means an efficacy which corresponds to that of the control, whereas an efficacy of 100% means that no infection is observed.

In this test, the substances according to the invention mentioned in Examples (1), (2), (3), (4), (5), (6), (7), (9), (10), (11), (13), (14), (15), (17), (19), (20), (34), (48), (50), (51), (53) and (59) show, at an application rate of 100 g/ha, an efficacy of 90% or more.

TABLE D

Plasmopara test (grapevine)/protective

| Active compound | Application rate of active compound in g/ha | Efficacy in % |
|---|---|---| according to the invention

| (1) | 100 | 90 |
| (2) | 100 | 100 |
| (3) | 100 | 91 |

TABLE D-continued

Plasmopara test (grapevine)/protective

| Active compound | Application rate of active compound in g/ha | Efficacy in % |
|---|---|---|
| (4) [structure] | 100 | 90 |
| (5) [structure] | 100 | 97 |
| (6) [structure] | 100 | 97 |
| (7) [structure] | 100 | 100 |

Example E
Sphaerotheca test (cucumber)/protective

Solvent: 47 parts by weight of acetone

Emulsifier: 3 parts by weight of alkylaryl polyglycol ether

To prepare a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of *Sphaerotheca fuliginea*. The plants are then placed in a greenhouse at approximately 23° C. and a relative atmospheric humidity of approximately 70%.

Evaluation is carried out 10 days after the inoculation. 0% means an efficacy which corresponds to that of the control, while an efficacy of 100% means that no infection is observed.

In this test, the substances according to the invention mentioned in Examples (1), (2), (3) and (4) show, at an application rate of 100 g/ha, an efficacy of 90% or more.

TABLE E

Sphaerotheca test (cucumber)/protective

| Active compound | Application rate of active compound in g/ha | Efficacy in % |
|---|---|---|
| according to the invention | | |
| (2) | 100 | 100 |
| (3) | 100 | 98 |
| (1) | 100 | 98 |
| (4) | 100 | 90 |

Example F

Venturia test (apple)/protective

Solvent: 47 parts by weight of acetone

Emulsifier: 3 parts by weight of alkylaryl polyglycol ether

To prepare a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rates. After the spray coating has dried on, the plants are inoculated with aqueous conidia suspension of the causative organism of apple scab *Venturia inaequalis* and then remain in an incubation cabin at approximately 20° C. and 100% relative atmospheric humidity for 1 day.

The plants are then placed in a greenhouse at approximately 21° C. and a relative atmospheric humidity of approximately 90%.

Evaluation is carried out 12 days after the inoculation. 0% means an efficacy which corresponds to that of the control, while an efficacy of 100% means that no infection is observed.

In this test, the substances according to the invention mentioned in Examples (2), (3), (4), (5), (7), (10), (11), (12), (13), (17), (20), (21), (22), (23), (24), (31), (36), (40), (48) and (59) show, at an application rate of 10 g/ha, an efficacy of 90% or more.

TABLE F

Venturia test (apple)/protective

| Active compound | Application rate of active compound in g/ha | Efficacy in % |
|---|---|---|
| according to the invention | | |
| (2) | 10 | 96 |
| (3) | 10 | 92 |
| (4) | 10 | 95 |
| (5) | 10 | 99 |
| (7) | 10 | 98 |

Example G
Pyricularia test (rice)/protective

Solvent: 2.5 parts by weight of acetone

Emulsifier: 0.06 parts by weight of alkylaryl polyglycol ether

To produce a suitable preparation of active compound, 1 part by weight of active compound is mixed with the stated amount of solvent, and the concentrate is diluted with water and the stated amount of emulsifier to the desired concentration.

To test for protective activity, young rice plants are sprayed with the preparation of this compound at the stated application rate. After the spray coating has dried on, the plants are inoculated with an aqueous spore suspension of *Pyricularia oryzae*. The plants are subsequently placed in a greenhouse at 100% relative atmospheric humidity and 25° C.

Evaluation is carried out 4 days after the inoculation. 0% means an efficacy which corresponds to that of the control, while an efficacy of 100% means that no infection is observed.

In this test, the substances according to the invention mentioned in Examples (1), (3), (4) and (7) show, at an application rate of 750 g/ha, an efficacy of 90% or more.

TABLE G

Pyricularia test (rice)/protective

| Active compound | | Application rate of active compound in g/ha | Efficacy in % |
|---|---|---|---|
| according to the invention: | | | |
| 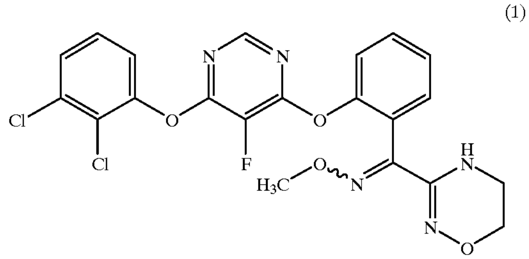  | (1) | 750 | 90 |
| 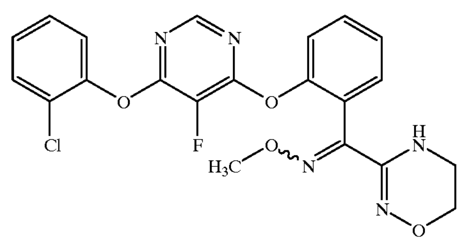  | (3) | 750 | 90 |
| 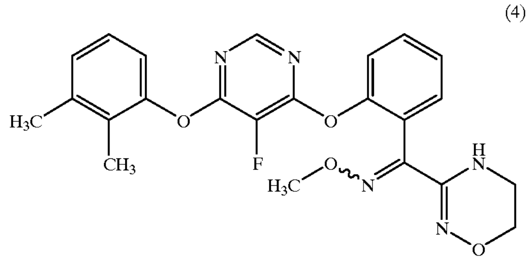  | (4) | 750 | 100 |
| 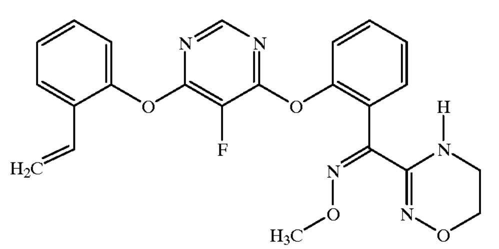  | (7) | 750 | 100 |

What is claimed is:

1. A compound of the formula (I)

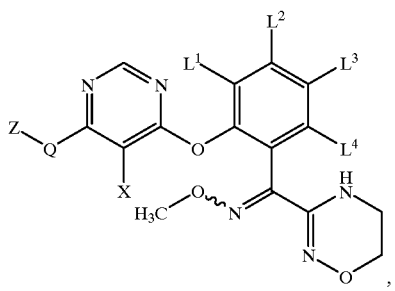

wherein

Z represents a moiety selected from the group consisting of cycloalkyl having 3 to 7 carbon atoms in the cycloalkyl moiety or cycloalkylalkyl having 3 to 7 carbon atoms in the cycloalkyl moiety and 1 to 4 carbon atoms in the alkyl moiety, with said cycloalkyl or cycloalkylalkyl being in each case optionally mono- to pentasubstituted by halogen or alkyl;

a heterocyclyl group selected from the group consisting of thienyl, pyridyl, furyl, thienylmethyl, pyridylmethyl or furylmethyl, each of which is optionally substituted by halogen, dialkylamino or alkyl having 1 to 4 carbon atoms;

an aryl or arylalkyl having in each case 6 to 10 carbon atoms in the aryl moiety and 1 to 4 carbon atoms in the alkyl moiety and being in each case optionally mono- to tetrasubstituted in the aryl moiety by identical or different substituents, the possible substituents being selected from the list below:

halogen, cyano, nitro, amino, formyl, carbamoyl, thiocarbamoyl;

alkyl, alkoxy, alkoxyalkyl, alkylthioalkyl, alkylaminoalkyl, dialkylaminoalkyl, alkylthio, alkylsulphinyl or alkylsulphonyl having in each case 1 to 8 carbon atoms and being in each case straight-chain or branched;

alkenyl or alkenyloxy having in each case 2 to 6 carbon atoms and being in each case straight-chain or branched;

halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms and being in each case straight-chain or branched;

halogenoalkenyl or halogenoalkenyloxy having in each case 2 to 6 carbon atoms and 1 to 11 identical or different halogen atoms and being in each case straight-chain or branched;

alkylamino, dialkylamino, alkylcarbonyl, alkoxycarbonyl, alkylaminocarbonyl, dialkylaminocarbonyl, dialkylaminocarbonyl, arylalkylaminocarbonyl, alkenylcarbonyl or alkinylcarbonyl having 1 to 6 carbon atoms in the hydrocarbon chains and being in each case straight-chain or branched;

cycloalkyl or cycloalkyloxy having in each case 3 to 6 carbon atoms;

a divalent group selected from the group consisting of alkylene having 3 or 4 carbon atoms, oxyalkylene having 2 or 3 carbon atoms or dioxyalkylene having 1 or 2 carbon atoms, wherein each end of said divalent group is attached to said aryl or arylalkyl and wherein each of said divalent groups is optionally mono- to tetrasubstituted by identical or different substituents selected from the group consisting of fluorine, chlorine, oxo, methyl, trifluoromethyl and ethyl; and a grouping

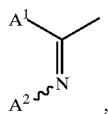

wherein $A^1$ represents hydrogen or alkyl having 1 to 4 carbon atoms or cycloalkyl having 3 to 6 carbon atoms and $A^2$ represents hydroxyl, amino, methyl, phenyl, benzyl, alkoxy, alkylamino, dialkylamino having 1 to 4 carbon atoms in the alkyl group, Q represents oxygen or sulphur, X represents halogen and $L^1$, $L^2$, $L^3$ and $L^4$ are identical or different and, independently of one another, each represents hydrogen, halogen, cyano, nitro, or represent alkyl, alkoxy, alkylthio, alkylsulphinyl or alkylsulphonyl, each of which is optionally substituted by halogen.

2. A compound of the formula (I) according to claim 1, in which

Z represents cyclobutyl, cyclopentyl or cyclohexyl, each of which is optionally mono- to pentasubstituted by fluorine, chlorine, methyl or ethyl;

represents thienyl, pyridyl, furyl, thienylmethyl, pyridylmethyl or furylmethyl, each of which is optionally substituted by methyl, ethyl, dimethylamino, fluorine, chlorine or bromine;

or represents phenyl or benzyl, each of which is optionally mono- to tetrasubstituted by identical or different substituents, the possible substituents being selected from the list below:

fluorine, chlorine, bromine, cyano, nitro, amino, formyl, carbamoyl, thiocarbamoyl, methyl, ethyl, n- or i-propyl, n-, i-, s- or t-butyl, methoxymethyl, methoxy, ethoxy, n- or i-propoxy, methylthio, ethylthio, n- or i-propylthio, methylsulphinyl, ethylsulphinyl, methylsulphonyl or ethylsulphonyl, methylaminomethyl, dimethylaminomethyl, vinyl, allyl, 2-methylallyl, propen-1-yl, crotonyl, propargyl, vinyloxy, allyloxy, 2-methylallyloxy, propen-1-yloxy, crotonyloxy, propargyloxy;

trifluoromethyl, trifluoroethyl, difluoromethoxy, trifluoromethoxy, difluorochloromethoxy, trifluoroethoxy, pentafluoroethoxy, 2-chloro-1,1,2-trifluoroethoxy, difluoromethylthio, trifluoromethylthio, difluorochloromethylthio, trifluoromethylsulphinyl or trifluoromethylsulphonyl, methylamino, ethylamino, n- or i-propylamino, dimethylamino, diethylamino, acetyl, propionyl, methoxycarbonyl, ethoxycarbonyl, methylaminocarbonyl, ethylaminocarbonyl, dimethylaminocarbonyl, diethylaminocarbonyl, acryloyl, propioloyl, cyclopentyl, cyclohexyl, propanediyl, ethyleneoxy, methylenedioxy, ethylenedioxy, each of which is doubly attached and each of which is optionally mono- to tetrasubstituted by identical or different substituents selected from the group consisting of fluorine, chlorine, oxo, methyl or trifluoromethyl,
or a grouping

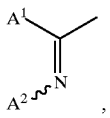

where
A$^1$ represents hydrogen or methyl and
A$^2$ represents hydroxyl, methoxy, ethoxy, amino, methylamino, methyl, phenyl or benzyl,
Q represents oxygen or sulphur,
X represents fluorine or chlorine, in particular fluorine, and
L$^1$, L$^2$, L$^3$ and L$^4$ are identical or different and, independently of one another, each represents hydrogen, fluorine, chlorine, bromine, cyano, nitro, methyl, ethyl, n- or i-propyl, n-, i-, s- or t-butyl, methoxy, ethoxy, n- or i-propoxy, methylthio, ethylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl.

3. The compound of claim 1 wherein X represents fluorine, chlorine or bromine and each of the alkyl groups of L$^1$, L$^2$, L$^3$ and L$^4$ has 1 to 6 carbon atoms and being in each case is optionally substituted by 1 to 5 halogen atoms.

4. A compound of the formula (II)

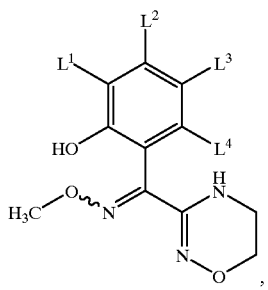

(II)

in which
L$^1$, L$^2$, L$^3$ and L$^4$ are each as defined in claim 1.

5. A compound of the formula (VI)

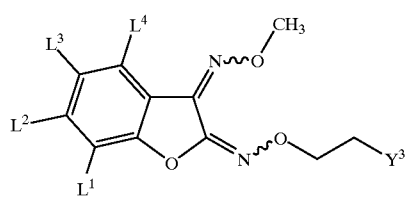

(VI)

in which
L$^1$, L$^2$, L$^3$ and L$^4$ are each as defined in claim 1 and
Y$^3$ represents halogen, alkylsulphonyl or arylsulphonyl.

6. A compound of the formula (IV)

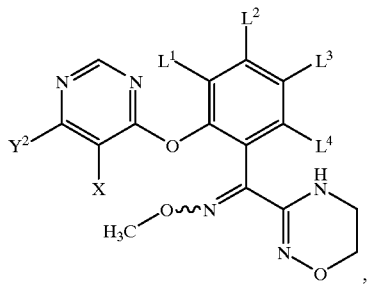

(IV)

in which

X, L$^1$, L$^2$, L$^3$ and L$^4$ are each as defined in claim 1 and
Y$^2$ represents halogen.

7. A composition having microbicidal activity comprising one or more compounds of claim 1 and one or more extenders and/or surfactants.

8. A process for preparing a compound of the formula (I), comprising the step of:

a) reacting a 3-(2-hydroxy-phenyl)-3-methoxyiminomethyl-oxadiazine of the formula (II),

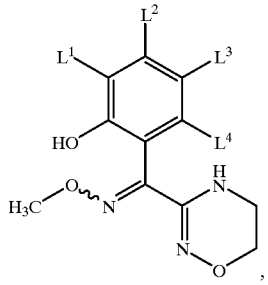

(II)

wherein
L$^1$, L$^2$, L$^3$ and L$^4$ are each as defined in claim 1 with a substituted halogenopyrimidine of the general formula (III),

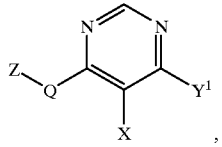

(III)

wherein
Z, Q and X are each as defined in claim 1 and
Y$^1$ represents halogen, if appropriate in the presence of a diluent, if appropriate in the presence of an acid acceptor and if appropriate in the presence of a catalyst, or b) reacting a phenoxypyrimidines of the general formula (IV)

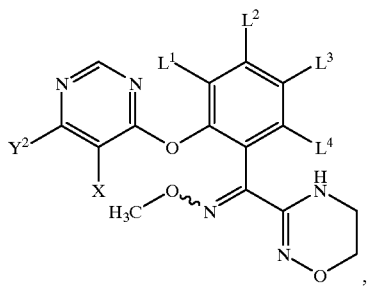
(IV)

wherein

X, $L^1$, $L^2$, $L^3$ and $L^4$ are each as defined in claim 1 and $Y^2$ represents halogen with a ring compound of the general formula (V),

Z—Q—H (V)

wherein

Z and Q are each as defined in claim 1.

9. A method for controlling undesirable microorganisms comprising applying an microbicidally effective amount of the compound of claim 1 to said microorganisms and/or their habitat.

10. A process for preparing a composition having microbicidal activity comprising mixing the compound of claim 1 with extenders and/or surfactants.

* * * * *